United States Patent
Barg et al.

(10) Patent No.: US 9,822,223 B2
(45) Date of Patent: Nov. 21, 2017

(54) METHOD OF PREPARING A COMPOSITION BASED ON HYALURONIC ACID

(71) Applicant: MERZ PHARMA GmbH & CO. KGaA, Frankfurt am Main (DE)

(72) Inventors: Heiko Barg, Weinheim (DE); Josef Friedrich, Köln (DE); Wolfgang Liebetrau, Friedberg (DE); Robert Voigts, Wind Lake, WI (US); Tim Stephen Ligman, Mundelein, IL (US)

(73) Assignee: MERZ PHARMA GmbH & Co. KGaA, Frankfurt am Main (DE)

( * ) Notice: Subject to any disclaimer, the term of this patent is extended or adjusted under 35 U.S.C. 154(b) by 112 days.

(21) Appl. No.: 14/407,231

(22) PCT Filed: Jun. 14, 2013

(86) PCT No.: PCT/EP2013/001782
§ 371 (c)(1),
(2) Date: Dec. 11, 2014

(87) PCT Pub. No.: WO2013/185934
PCT Pub. Date: Dec. 19, 2013

(65) Prior Publication Data
US 2015/0232623 A1    Aug. 20, 2015

Related U.S. Application Data

(60) Provisional application No. 61/660,269, filed on Jun. 15, 2012.

(30) Foreign Application Priority Data

Jul. 4, 2012 (EP) ..................... 12004962
Feb. 26, 2013 (EP) ..................... 13000961

(51) Int. Cl.
| | |
|---|---|
| *A61K 9/14* | (2006.01) |
| *C08L 5/08* | (2006.01) |
| *C08J 3/075* | (2006.01) |
| *C08J 3/24* | (2006.01) |
| *A61L 27/20* | (2006.01) |
| *A61L 27/54* | (2006.01) |
| *A61L 27/52* | (2006.01) |
| *A61K 9/70* | (2006.01) |
| *A61K 31/16* | (2006.01) |

(52) U.S. Cl.
CPC .............. *C08J 3/075* (2013.01); *A61L 27/20* (2013.01); *A61L 27/52* (2013.01); *A61L 27/54* (2013.01); *C08J 3/24* (2013.01); *C08L 5/08* (2013.01); *A61L 2400/06* (2013.01); *A61L 2430/34* (2013.01); *C08J 2305/08* (2013.01)

(58) Field of Classification Search
None
See application file for complete search history.

(56) References Cited

U.S. PATENT DOCUMENTS

| | | |
|---|---|---|
| 4,713,448 A | 12/1987 | Balazs |
| 4,920,194 A | 4/1990 | Feller |
| 8,052,990 B2 | 11/2011 | Hermitte |
| 2006/0194758 A1 | 8/2006 | Lebreton |
| 2010/0316683 A1 | 12/2010 | Piron |
| 2011/0166530 A1 | 7/2011 | Kreiner |

FOREIGN PATENT DOCUMENTS

| | | | |
|---|---|---|---|
| EP | EP0466300 | 1/1992 | |
| WO | WO93/15117 | 8/1993 | |
| WO | WO97/04012 | 2/1997 | |
| WO | WO2005066215 | 7/2005 | |
| WO | WO2009/073437 | 6/2009 | |
| WO | WO2009/098127 | 8/2009 | |
| WO | WO 2010/015900 | 2/2010 | |
| WO | WO 2010/015901 | 2/2010 | |
| WO | WO2010/105900 | 2/2010 | |
| WO | WO2010/115081 | 10/2010 | |
| WO | WO 2011/023355 A2 * | 3/2011 | ............. A61L 27/26 |
| WO | WO2011/119468 | 9/2011 | |
| WO | WO2012/062775 | 5/2012 | |

OTHER PUBLICATIONS

International Search Report for PCT/EP2013/001782 on Sep. 11, 2013.
Emervel, formulated with or without lidocaine, 2011, pp. 1-2.
Emervel, Product Summary 2011, pp. 1-4.
Patterns of proteoglycan synthesis during chondrogenesis; Extracellular Matrix, edited by Susan Hawkes and John Wang, 1982, Academic Press, pp. 73.
Segura, S., et al., "A complete range of hyaluronic acid filler with distinctive physical properties specifically designed for optimal tissue adaptations", J Drugs Dermatol., Jan. 2012, 11(1 Suppl):s5-8.

* cited by examiner

*Primary Examiner* — Jeffrey T. Palenik
(74) *Attorney, Agent, or Firm* — Hueschen and Sage

(57) ABSTRACT

The invention relates to a method of preparing a composition, the composition comprising a crosslinked first polymer, optionally a second polymer, which may be crosslinked or non-crosslinked, and water, wherein the first and the second polymer are selected from a polysaccharide, comprising at least steps (i) to (iv):
 (i) crosslinking a mixture comprising the first polymer and water;
 (ii) subsequent to the crosslinking in step (i), terminating the crosslinking;
 (iii) optionally blending the product obtained in step (ii) with the second polymer;
 (iv) subjecting the product obtained in step (iii) to dialysis.

11 Claims, No Drawings

METHOD OF PREPARING A COMPOSITION BASED ON HYALURONIC ACID

FIELD OF THE INVENTION

The invention relates to a method of preparing a composition, such as a gel, based on a polysaccharide, such as hyaluronic acid, to the composition as such, to a kit comprising a syringe and the composition, and to the use of the composition as a dermatological filler.

BACKGROUND OF THE INVENTION

It is known to use gels such as hydrogels based on polysaccharides and water as dermatological fillers. Such gels are generally prepared by methods comprising the chemical cross-linking of the respective polysaccharides in an aqueous medium. Suitable polysaccharides are e.g. based on hyaluronic acid since it is present in identical or similar compositions in each living organism. E.g., hyaluronic acid is a major component of skin, where it is involved in tissue repair. Therefore, it gives a minimum of side effects and allows for safe application.

EP 1 818 344 relates to a process for preparing a cross-linked hyaluronic acid gel, comprising stirring and mixing a mixture containing 10 w/v % or more of hyaluronic acid, a crosslinking agent, and water under acidic or alkaline condition.

EP 2 054 039 (WO 2008/018796) relates to a viscoelastic hydrogel composition comprising first microparticles and second microparticles capable of interacting with each other through stereocomplex interactions, wherein said first microparticles comprise a crosslinked first hydrophilic polymer, said first microparticles comprising external grafts of first oligomers or co-oligomers comprising a first chiral region, said first chiral region comprising first chiral monomers, and wherein said second microparticles comprise a crosslinked second hydrophilic polymer, said second microparticles comprising external grafts of second oligomers or co-oligomers comprising a second chiral region, said second chiral region comprising second chiral monomers, said second chiral monomers having chirality that is opposite to the chirality of said first chiral monomers, wherein said first chiral region and said second chiral region interact with each other non-covalently. The hydrophilic polymer may be hyaluronic acid.

EP 2 178 923 (WO 2009/018076) relates to a process for the preparation of crosslinked hyaluronic acid, said process comprising contacting hyaluronic acid with a polyethylene glycol based crosslinking agent.

WO 2011/119468 relates to a hydrogel for soft tissue augmentation comprising a cross-linked biocompatible polymer having zero-length cross-linked moieties and optionally at least one other active ingredient incorporated into said cross-linked biocompatible polymer.

EP 2 152 329 (WO 2008/068297) relates to an implant that can be injected subcutaneously or intradermally in the form of a single-phase hydrogel comprising a gel composed of crosslinked hyaluronic acid and one of its physiologically acceptable salts.

EP 2 170 961 (WO 2009/021526) relates to a hyaluronic acid dispersion for use in aesthetics medicine and orthopedics, wherein the dispersed phase comprises particles made of crosslinked hyaluronic acid, and the continuous phase substantially comprises linear hyaluronic acid.

EP 1 699 500 (WO 2005/067994) relates to a hyaluronic acid composition comprising crosslinked, water-insoluble, hydrated hyaluronic acid gel particles. The composition may be used for augmenting tissue in a subject that is in need of tissue augmentation, to a method of stabilizing crosslinked HA including hydrating water-insoluble, dehydrated cross-linked HA with a physiologically compatible aqueous solution that includes a local anesthetic, wherein the value of storage modulus G' for the stabilized composition is at least about 110% of the value of G' for a non-stabilized composition, and to the stabilized HA composition.

WO 2010/015900 relates to soft tissue fillers, for example, dermal and subdermal fillers, based on hyaluronic acids and pharmaceutically acceptable salts thereof, wherein the hyaluronic acid-based compositions may include a therapeutically effective amount of at least one anesthetic agent, for example, lidocaine. The hyaluronic acid-based compositions including lidocaine have an enhanced stability, relative to conventional compositions including lidocaine, for example when subjected to sterilization techniques or when stored for long periods of time. Methods and processes of preparing such hyaluronic acid-based compositions are also provided.

FR 2 919 999 relates to a cosmetical composition or pharmaceutical composition, which comprises a hyaluronic acid and a divalent cation. The composition may be used for treating wrinkles.

EP 2 254 584 (WO 2009/098127) relates to biocompatible injectable products capable of releasing zinc and/or at least one saccharide salt in the form of zinc, to compositions containing said products, and to the use thereof in particular for filling or increasing the volume of biological tissues or for replacing or supplementing a biological fluid.

EP 2 155 212 (WO 2008/139122) relates to the association of hyaluronic acid and at least one inhibitor of hyaluronic acid degradation, which is intended, in particular, for use in human dermatology and plastic surgery.

EP 0 839 159 B1 discloses a process for preparing a cross-linked biocompatible polysaccharide gel composition. The process comprises the cross-linking of a polysaccharide in the presence of polyfunctional cross-linking agents, wherein a viscoelastic gel is formed.

EP 1 711 552 B1 relates a method for producing a biocompatible crosslinked gel comprising steps of crosslinking a biocompatible polymer, diluting the crosslinked polymer with non-crosslinked polymer, and terminating the crosslinking reaction.

EP 0 466 300 B1 relates to a method of obtaining a biocompatible viscoelastic gel slurry, the method comprising the mixing of a biocompatible gel, which comprises crosslinked hyaluronic acid, with a second polymer, which may e.g. be hyaluronic acid, to form a two phase mixture, and to the gel as such.

OBJECTS OF THE INVENTION

One object of the invention is to provide a process for the preparation of a composition, such as a gel, based on a polysaccharide, which may be used as a dermatological filler, wherein the composition should have an excellent stability, i.e. does not change its properties, in particular its viscoelastic properties, after application, and which may be adjusted in a tailor-made manner to dermatological requirements. Furthermore, the gel should have excellent compatibility with skin tissue.

SUMMARY OF THE INVENTION

This object is achieved with a method of preparing a composition, such as a gel, the composition comprising a cross-linked first polymer, optionally a second polymer, which may be crosslinked or non-crosslinked, and water, wherein the first and the second polymer are selected from a polysaccharide; and with the composition prepared according to said method.

Specifically, according to a first aspect, the invention relates to a method of preparing a composition, such as a gel, the composition comprising a crosslinked first polymer, optionally a second polymer, the second polymer may be crosslinked or non-crosslinked, and water, wherein the first and the second polymer are selected from a polysaccharide, the method comprising at least steps (i) to (iv):

(i) crosslinking a mixture comprising the first polymer and water;
(ii) subsequent to the crosslinking in step (i), terminating the crosslinking;
(iii) optionally blending the product obtained in step (ii) with the second polymer;
(iv) subjecting the product obtained in step (ii) or step (iii) to dialysis.

In one embodiment, the presence of the second polymer is mandatory. In this embodiment, the method requires the blending of the product obtained in step (ii) with the second polymer according to step (iii).

In one embodiment, the presence of the second polymer is not necessary. In this embodiment, the method does not require the blending of the product obtained in step (ii) with the second polymer according to step (iii).

In one embodiment, the first and the second polymer may be the same.

In one embodiment, the first and the second polymer may be different from one another.

In one embodiment, the first polymer is crosslinked and the second polymer is non-crosslinked.

In one embodiment, the first and the second polymer are selected from a hyaluronic acid and a salt thereof.

In one embodiment, the first and the second polymer are selected from a hyaluronic acid or a salt thereof.

In one embodiment, the salt of hyaluronic acid is a sodium salt.

In one embodiment, the first polymer employed in step (i) has a molecular weight Mw of from 1.5 MDa to less than 3.5 MDa, or from 2.0 MDa to less than 3.5 MDa, or from 2.5 MDa to less than 3.0 MDa.

In one embodiment, the second polymer employed in step (iii) has a molecular weight of at least 3.0 MDa, or at least 3.5 MDa.

In one embodiment, the weight of the second polymer based on the weight of the first polymer is less than 5%, or less than 4%, e.g. is in the range of from 0.01 to 5%, or is in the range of from 0.1 to 4%, or is in the range of from 0.1 to 2.5%, or from 0.2 to 2.0%, or from 0.5 to 1.5%.

In one embodiment, the method comprises after step (iv) a further step (v):
(v) admixing an anesthetic or anti-arrhythmic, such as lidocaine, or lidocaine hydrochloride, or lidocaine hydrochloride monohydrate, or tetracaine, to the product obtained in step (iv).

In one embodiment, the method comprises after step (iv), or after step (v), a further step (vi):
(vi) filling the product obtained in step (iv) or step (v) into a syringe and sterilizing it.

In one embodiment, the mixture of step (i) further comprises an alkaline phosphate buffer.

In one embodiment, said second polymer is provided in step (iii) in the form of a mixture with a phosphate buffer.

In one embodiment, said anesthetic or anti-arrhythmic, such as lidocaine or tetracaine provided in step (v), is provided in the form of a mixture with a phosphate buffer.

In one embodiment, the reaction temperature in step (i) is from 0 to 40° C., e.g. from 15 to 40° C.; or from 25 to 35° C., or from 25 to 30° C.; or from 30 to 35° C.

In one embodiment, the reaction temperature in step (ii) is from 0 to 30° C., e.g. from 0 to 10° C.; or from 3 to 7° C.

In one embodiment, the reaction temperature in step (iii) is from 0 to 30° C., e.g. from 0 to 10° C.; or from 3 to 7° C.

In one embodiment, the reaction temperature in step (iv) is from 0 to 30° C., e.g. from 0 to 10° C.; or from 3 to 7° C.

In one embodiment, in step (i), a diglycidyl ether is used as crosslinking agent.

In one embodiment, in step (i), 1,4-butanediol diglycidyl ether (BDDE) is used as crosslinking agent.

In one embodiment, step (ii) comprises step (ii.1):
(ii.1) subjecting the product obtained in step (i) to an acid.

In one embodiment, step (ii) comprises steps (ii.1) and (ii.2):
(ii.1) subjecting the product obtained in step (i) to an acid;
(ii.2) extruding the product obtained in step (ii.1); or
extruding the product obtained in step (ii.1) through a sieve; or
extruding the product obtained in step (ii.1) through a sieve having a mesh size in the range of from 500 to 600 μm.

In one embodiment, said dialysis step according to step (iv) further comprises steps (iv.1) to (iv.3):
(iv.1) extruding the product obtained in step (iii) through a first sieve and subsequently extruding the extruded product from the first sieve through a second sieve, wherein the mesh size of the second sieve is less than the mesh size of the first sieve; or
extruding the product obtained in step (iii) through a first sieve, and subsequently extruding the extruded product from the first sieve through a second sieve, and subsequently extruding the extruded product from the second sieve through a third sieve, wherein the mesh size of the second sieve is less than the mesh size of the first sieve, and the mesh size of the third sieve is less than the mesh size of the second sieve;
(iv.2) filling the product obtained in step (iv.1) into a dialysis membrane;
(iv.3) subjecting the filled membrane obtained in step (iv.2) to a dialysis solution.

In one embodiment, said dialysis step according to step (iv) further comprises steps (iv.1) to (iv.3):
(iv.1) extruding the product obtained in step (iii) through a first sieve having a mesh size in the range of from 325 to 425 μm; and subsequently extruding the extruded product from the first sieve through a second sieve having a mesh size in the range of from 175 to 225 μm; and subsequently extruding the extruded product from the second sieve through a third sieve having a mesh size in the range of from 110 to 170 μm;
(iv.2) filling the product obtained in step (iv.1) into a dialysis membrane having a molecular weight cut off in the range of from 12,000 to 14,000 Da;
(iv.3) subjecting the filled membrane obtained in step (iv.2) to a dialysis solution.

Any embodiment of the above embodiments may be combined with at least one further embodiment selected from the above embodiments.

According to a second aspect, the invention relates to a composition, such as a gel, the composition comprising a crosslinked first polymer, optionally a second polymer, the second polymer may be crosslinked or non-crosslinked, and water, wherein the first and the second polymer are selected from a polysaccharide, obtainable by the method according to the first aspect, or according to the method of the first aspect and any embodiment or any combination of at least two embodiments defined therein.

According to a third aspect, the invention relates to a kit, the kit comprising a syringe and the composition according to the second aspect, or the composition prepared according to the method according to the first aspect.

According to a fourth aspect, the invention relates to the use of the composition according to the second aspect, or to the use of the composition prepared according to the first aspect, in a cosmetic application.

In one embodiment, the composition is used as a dermatological filler.

According to a fifth aspect, the invention relates to a composition such as a gel according to the second aspect for use as a medicament.

DETAILED DESCRIPTION OF THE INVENTION

According to the first aspect, the invention relates to a method of preparing a composition comprising a crosslinked first polymer, optionally a second polymer, which may be crosslinked or non-crosslinked, and water, wherein the first and the second polymer are selected from a polysaccharide, the method comprising at least steps (i) to (iv):
(i) crosslinking a mixture comprising the first polymer and water;
(ii) subsequent to the crosslinking in step (i), terminating the crosslinking;
(iii) optionally blending the product obtained in step (ii) with the second polymer;
(iv) subjecting the product obtained in step (ii) or step (iii) to dialysis.

The term "composition" as used in this disclosure encompasses a product comprising the crosslinked first polymer, optionally the second polymer, which may be crosslinked or non-crosslinked, and water.

In one embodiment, the composition is a gel such as a hydrogel. The term "gel" as used herein encompasses a product, which has both viscous and elastic properties. Thus, the term encompasses a viscoelastic product. In popular science, a gel sometimes is characterized as a jelly-like material. The viscoelastic properties of a gel may be determined by determining the loss modulus and the storage modulus of the gel.

The ratio between the loss module G" and the storage module G' may be expressed by the loss factor tan $\delta$=G"/G'. The higher the loss factor, the more the properties of the product approach Newtonian flow. The viscosity of the product may be expressed in terms of $\eta^*$. Suitable methods for determining tan $\delta$ and $\eta^*$ are known in the art.

The composition or the composition such as the gel according to the invention mandatorily requires the use of a polysaccharide as the first, and if a second polymer is used also the use of a polysaccharide as the second polymer, in the method of the invention.

The term "polysaccharide" as used herein encompasses a carbohydrate molecule consisting or comprising repeated monomer units joint together by glycosidic bonds. In general, the polysaccharide contains more than 10 monosaccharide units. Examples of a polysaccharide are polysaccharides such as starch, glycogens, cellulose, chitin, or hyaluronic acid, or mixtures thereof.

In a preferred embodiment, the polysaccharide is a hyaluronic acid. The hyaluronic acid may be provided in the form of a salt thereof such as the sodium salt. It is also possible to provide a mixture of the acid and a salt thereof such as the sodium salt.

Thus, the term "hyaluronic acid" as used herein is synonymously used to terms such as "hyaluronan" or "hyaluronate". In the following, hyaluronic acid may be abbreviated with the term "HA".

HA is a non-crosslinked polymer of disaccharides. It can have up to 25.000 disaccharide units in length. The molecular weight of HA may range from 5,000 to 20,000,000 Da.

HA has a well recognized meaning in the art. It is commercially available in grades having different molecular weights (Mw) and/or different molecular weight distributions. It is available in non-crosslinked form as is used as starting material in step (i) of the method according to the invention.

Step (i)

Step (i) requires the crosslinking of a mixture comprising the first polymer and water.

The term "crosslinking" as used herein encompasses the linking of at least two different polymer chains of the polysaccharide by means of a chemical bond or chemical bonds. As a consequence, molecular weight of the first polymer is increased, and thus viscosity and/or elasticity.

In one embodiment, crosslinking is performed via a crosslinker.

Suitable crosslinker for crosslinking polysaccharides such as hyaluronic acids are known in the art.

In one embodiment, a crosslinker based on an epoxide-structure may be used in the method according to the invention.

In one embodiment, a diglycidyether is used for the crosslinking.

In one embodiment, 1,4-butanediol diglycidylether (BDDE) is used for the crosslinking. This compound is commercially available.

In one embodiment, the crosslinker is used in a quantity of from 5 to 15% (volume crosslinker/weight of hyaluronic acid), such as 6 to 14% (v/w), or 7 to 12% (v/w).

Advantageously, the temperature in the crosslinking reaction according to step (i) is controlled.

In one embodiment, crosslinking according to step (i) is effected in a temperature range of from 0 to 40° C.

In another embodiment, the temperature in step (i) is controlled such that it proceeds in a temperature range of from 15 to 40° C.

In one embodiment, the temperature in step (i) is from 25 to 35° C.

In one embodiment, the temperature in step (i) is controlled such that the crosslinking proceeds in a temperature range of from 25 to 30° C.

In another embodiment, the temperature in step (i) is controlled such that the crosslinking proceeds in a temperature range of from 30 to 35° C., or from above 30° C. to 35° C.

Such temperatures or temperature ranges may ensure a very homogenous crosslinking avoiding inhomogeneous particles as far as possible. Furthermore, in one embodiment, the control of the temperature allows the tailor-made adjustment of the viscoelastic properties of the composition according to the invention.

In one embodiment, if the crosslinking according to step (i) is performed at a higher temperature, e.g. in a temperature range of from above 30 to 35° C., the viscoelastic properties of the resulting composition such as a gel is more intense compared to composition, in which the crosslinking has been performed at a lower temperature, e.g. at a temperature of from 25° C. to 30° C. Such differences may be characterized by determining the storage modulus and the loss modulus of the composition according to methods known in the art. Accordingly, in one embodiment, the appropriate selection of the reaction temperature in step (i) allows for the preparation of compositions such as gels having different viscoelastic properties.

The term "mixture" as used herein encompasses a combination of two or more substances, which are mixed but not chemically bound to one another. Thus, the term "mixture" refers to a physical combination of the first polymer, which is a polysaccharide, and water. The mixture may be provided in the form of a solution, or a suspension, or a colloid.

The first polymer, i.e. the first polysaccharide, i.e. HA, in general has a molecular weight Mw in the range of from 1.0 to 4.0 MDa, or from 1.5 MDa to less than 3.5 MDa, or from 2.0 MDa to less than 3.5 MDa. These ranges of molecular weight Mw relate to ranges before crosslinking, respectively.

In one embodiment, the first polysaccharide has a molecular weight Mw of from 2.5 MDa to less than 3.0 MDa, again before crosslinking.

Water may be provided in the form of pipe water, distilled water, or deionised water.

In one embodiment, the mixture used in step (i) additionally comprises a buffer solution.

In one embodiment, the buffer solution is a phosphate buffer solution.

In one embodiment, said phosphate buffer solution is made from sodium chloride, dibasic anhydrous sodium phosphate, monobasic sodium phosphate dihydrate and water.

In one embodiment, the buffer is an alkaline buffer.

In one embodiment, the $p_H$ of the buffer is from 6.8 to 7.6, or from 7.0 to 7.4, or from 7.1 to 7.3.

In one embodiment, the $p_H$ of the final composition prepared according to the method of the invention is adjusted to a range of from 6.5 to 7.5 such as 6.7 to 7.2, or 6.8 to 7.1 or 6.8 to 6.9. Such $p_H$ may support the compatibility of the composition with skin tissue. For the adjustment of said $p_H$, in one embodiment, said buffer is used.

In one embodiment, step (i) may be effected by mixing the first polymer, water, the crosslinker, and optionally buffer solution, and stirring the mixture for a pre-determined time, wherein the temperature is controlled to not exceed the pre-determined setpoint.

Step (ii)

Step (ii) requires the termination of the crosslinking effected in step (i).

The termination of the crosslinking reaction according to step (ii) is manadatorily necessary since otherwise composition or gels may be obtained having a viscosity or a viscosity and elasticity being too high to allow for the appropriate use as dermatological filler, respectively the viscosity or the viscoelastic properties of the composition or gel are not constant as long as the gel contains compounds that may effect crosslinking such as the crosslinker used in step (i).

Basically, each compound capable of reacting with the crosslinker and thus deactivating it may be used for terminating the crosslinking reaction.

Since, in one embodiment, crosslinkers of the epoxide type are used in step (i), termination of the crosslinking may be effected by means of the addition of compounds, which cleave the epoxide moiety such that no further crosslinking with suitable groups in the polysaccharide can occur.

In one embodiment, cleavage of the epoxide and thus termination of the crosslinking in step (i) may be effected by an acid. Organic acids as well as inorganic acids may be used for terminating of crosslinking.

In one embodiment, an inorganic acid such as hydrochloric acid is used.

The compound used for termination of the crosslinking reaction may be applied in a buffer solution, e.g. in the buffer solution as used in step (i).

Such solution may be termed as "quench solution". Accordingly, termination according to step (ii) may be effected by quenching the crosslinked mixture obtained according to step (i).

In one embodiment, the termination of crosslinking according to step (ii) is effected in a temperature range of from 0° C. to 30° C.

In another embodiment, the temperature in step (ii) is controlled such that it does not exceed a temperature of 20° C., or 15° C.

In one embodiment, the temperature in step (ii) is from 0 to 10° C., or from 3 to 7° C., e.g. 5° C.

The termination according to step (ii) may be effected by adding the compound used for termination to the mixture according to step (i), and e.g. stirring it for a predetermined time.

The termination of the crosslinking reaction is crucial for the method according to the invention, since the thus obtained composition or gel has an excellent stability, i.e. it does not change its properties, in particular its viscosity or its viscoelastic properties, after application, e.g. after use as dermatological filler in the skin tissue.

In one embodiment, termination may further be supported by extruding in step (ii) the crosslinked product obtained in step (i), e.g. extruding the product through a sieve. Without being bound by theory, it is believed that the high shear forces applied during extrusion provide for a thoroughly mixing of the crosslinker and the compound used for the termination of the crosslinking reaction in the composition or gel. As a consequence, the crosslinker is completely or nearly completely inactivated, thus preventing further crosslinking and thus further undesired increase of molecular weight and viscosity and/or elasticity.

The term "extruding through a sieve" encompasses terms such as "passed through a sieve", or "pressed through a sieve" or "directed through a sieve" or "filtered".

Thus, in one embodiment, step (ii) comprises step (ii.1):
(ii.1) extruding the crosslinked product obtained in step (i).

In another embodiment, step (ii) comprises steps (ii.1) and (ii.2):
(ii.1) subjecting the product obtained in step (i) to an acid;
(ii.2) extruding the product obtained in step (ii.1); or extruding the product obtained in step (ii.1) through a sieve.

In another embodiment, step (ii) comprises steps (ii.1) and (ii.2):
(ii.1) subjecting the product obtained in step (i) to an acid;
(ii.2) extruding the product obtained in step (ii.1); or
extruding the product obtained in step (ii.1) through a sieve; or
extruding the product obtained in step (ii.1) through a sieve having a mesh size in the range of from 500 to 600 µm.

In one embodiment, the mesh size of the sieve used in step (ii.2) is approximately 560 µm, such as 558.8 µm (0.022").

Step (iii)

Optional Step (iii) requires the blending of the product obtained in step (ii) with the second polymer.

In one embodiment, the presence of the second polymer is not necessary, and thus step (iii) is omitted in the reaction sequence of steps (i) to (iv).

In another embodiment, the presence of the second polymer is necessary, and thus step (iii) is necessarily performed in the reaction sequence of steps (i) to (iv).

The term "blending" as used herein encompasses the mixing of the crosslinked polymer obtained in step (ii) with the second polymer used in step (iii), wherein the obtained blend comprising the crosslinked first polymer and the second polymer, which may also be crosslinked, however, may also be provided in non-crosslinked form, has different physical properties with respect to the first and to the second polymer.

The second polymer is a polysaccharide, too. This polymer may be the same polymer as the first polymer, or may be different therefrom.

Thus, in one embodiment, the second polymer is the same HA as the first polymer used in step (i), or is a HA that is different from the HA used in step (i).

In one embodiment, the first polymer has the same molecular weight as the second polymer. In another embodiment, the molecular weights are different from one another. The term "molecular weight" of said second polymer refers to the respective molecular weight of said polymer before blending and optionally crosslinking said second polymer.

In one embodiment, the second polymer has a molecular weight of at least 3.0 MDa, or of at least 3.5 MDa, or of at least 4.0 MDa.

In one embodiment, the second polymer has a molecular weight of at least 3.0 MDa, wherein the upper limit is 20 MDa, or 10 MDa, or 8 MDa, or 6 MDa, or 4 MDa, respectively.

In one embodiment, the second polymer has a molecular weight of at least 3.5 MDa, wherein the upper limit is 20 MDa, or 10 MDa, or 8 MDa, or 6 MDa, or 4 MDa, respectively.

In one embodiment, the second polymer has a molecular weight of at least 4.0 MDa, wherein the upper limit is 20 MDa, or 10 MDa, or 8 MDa, or 6 MDa, or 4 MDa, respectively.

In one embodiment, the second polymer is provided in a buffer such as the buffer, which may be used in step (i) or in step (ii).

In one embodiment, the blending according to step (iii) is effected in a temperature range of from 0° C. to 40° C., or from 0° C. to 30° C.

In another embodiment, the temperature in step (iii) is controlled such that it does not exceed a temperature of 20° C., or 15° C.

In one embodiment, the temperature in step (iii) is from 0 to 10° C., or from 3 to 7° C.; e.g. 5° C.

In one embodiment, blending according to step (iii) is performed by stirring the crosslinked product, wherein the crosslinking has been terminated according to step (ii), with the second polymer.

In one embodiment, the weight of the second polymer based on the weight of the first polymer is less than 5%, or less than 4%, e.g. is in the range of from 0.01 to 5%, or is in the range of from 0.1 to 4%, or is in the range of from 0.1 to 2.5%, or from 0.2 to 2.0%, or from 0.5 to 1.5%.

In one embodiment, step (iii) allows the tailor-made adjustment of properties with respect to viscosity and elasticity, or viscosity or elasticity of the target composition or gel, which are essential for the use as dermatological filler.

Such properties may be achieved by selecting a suitable temperature range such in step (i) and/or weight ratio between the first and the second polymer in step (iii) and/or quantity of crosslinker used in step (i) and optionally used for the second polymer, provided that second polymer is employed in step (iii) and is employed in crosslinked form.

Furthermore, the use of a second polymer in step (iii) may improve the flowability of the composition through a sieve, if a sieving step is performed. Then, in general, lower extrusion forces are necessary to extrude the composition through said sieve or sieves as compared to a composition not containing said second polymer. Moreover, the use of a second polymer in a non-crosslinked form may advantageously improve the flowability of the composition according to the invention through the needle of a syringe that is used to apply the composition in a cosmetic application. In turn, less force may used to extrude the composition through said needle.

Step (iv)

Step (iv) requires the subjection of the product obtained in step (ii) or (iii) to dialysis.

In one embodiment, this step serves for the removal of extraneous compounds or particles from the gel obtained in step (iii). Extraneous compounds or particles might negatively affect the physical properties of the composition such as a gel and/or might adversely affect the compatibility of the composition or gel with skin tissue. Thus, in one embodiment, step (iv) serves for the lowering or for the avoidance of possible inflammatory reactions when the composition according to the invention is injected into skin tissue.

In another embodiment, this step serves for adjusting the swelling of the gel obtained in step (ii) or step (iii).

The term "swelling" or "swellability" as used herein encompasses the water take-up of the gel.

In one embodiment, the swelling of the gel obtained in step (iii) when subjected to step (iv), i.e. the water-take up during dialysis, is from 5 to 25% based on the total weight of the gel such as from 6 to 23%, or from 7 to 22%, or from 9 to 21%.

In another embodiment, the swelling or swellability is from 7 to 18%, or from 8 to 15%.

In one embodiment, such swelling or swellability creates a swelling pressure that enables the HA matrix to withstand compressive forces, e.g. when injected into skin tissue and said skin tissue is exposed to compressive force.

In one embodiment, step (iv) serves for the removal of extraneous compounds or particles from the gel obtained in step (ii) or step (iii) and for adjusting the swelling of the gel obtained in step (ii) or step (iii).

Thus, step (iv) serves, among others, for the provision of a further improved HA composition as compared to products known in the art.

Thus, besides step (ii) (termination of the crosslinking), step (iv) (dialysis) is a further crucial reaction step in the sequence of steps required for the preparation of the composition such as a gel according to the invention. In particular the combination of step (ii) and step (iv) in the reaction sequence according to the invention allows the provision of a composition such as a gel having the properties, which should be achieved according to the posed problem.

In one embodiment, dialysis is performed using a dialysis membrane having a predetermined molecular weight cut off. Such dialysis membranes are commercially available The term "molecular weight cut off (MWCO)" as used herein refers to the lowest molecular weight solute (in Daltons) in which a defined percentage of the solute is retained by the membrane used for dialysis, or refers to the molecular weight at which a defined percentage of the analytes are prohibited from membrane diffusion.

Commercially available dialysis membranes typically have MWCOs that range from 1,000 to 100,000 Da.

In one embodiment, the used dialysis membrane has a MWCO in the range of from 12,000 to 14,000 Da.

In one embodiment, dialysis is performed using a dialysis solution comprising a buffer.

In one embodiment, the buffer is the buffer used in step (i), or used in step (ii), or used in step (iii).

In one embodiment, the dialysis according to step (iv) is effected in a temperature range of from 0° C. to 30° C.

In another embodiment, the temperature in step (iv) is controlled such that it does not exceed a temperature of 20° C., or 15° C.

In one embodiment, the temperature in step (iv) is from 0 to 10° C., or from 3 to 7° C., e.g. 5° C.

In one embodiment, the method according to the invention is performed such that the temperature in step (i) is from 25 to 35° C., and the temperature in steps (ii) to (iv) is from 0 to 10° C., respectively; or the method according to the invention is performed such that the temperature in step (i) is from 25 to 35° C., and the temperature in steps (ii) to (iv) is from 3 to 7° C., e.g. 5° C., respectively.

In one embodiment, prior to subjecting the product obtained in step (iii) to dialysis, the product may be subjected to a sieving step, or several sieving steps, in order to further homogenize the product, respectively to remove inhomogeneous particles or any further particles, which might negatively affect the use as dermatological filler.

In one embodiment, said dialysis step (iv) comprises steps (iv.1) to (iv.3):
(iv.1) extruding the product obtained in step (ii) or step (iii) through a first sieve and subsequently extruding the extruded product from the first sieve through a second sieve, wherein the mesh size of the second sieve is less than the mesh size of the first sieve; or
extruding the product obtained in step (ii) or step (iii) through a first sieve, and subsequently extruding the extruded product from the first sieve through a second sieve, and subsequently extruding the extruded product from the second sieve through a third sieve, wherein the mesh size of the second sieve is less than the mesh size of the first sieve, and the mesh size of the third sieve is less than the mesh size of the second sieve;
(iv.2) filling the product obtained in step (iv.1) into a dialysis membrane;
(iv.3) subjecting the filled membrane obtained in step (iv.2) to a dialysis solution.

Such use of sieves prior to dialysis may further support the efficacy of dialysis step. The appropriate selection of the mesh size of the sieves further supports the removal of extraneous compounds and particles such as gelled particles, which negatively affect the desired homogeneity of the product. Thus, in one embodiment, a sieving step or several sieving steps used in the method according to the invention allow for the preparation of a particularly homogeneous composition, i.e. a particularly homogeneous gel comprising the first polymer, optionally the second polymer, and water. Homogeneity is a desired property of the composition, which is obtained according to the method of the invention, and supports and improves the intended application such as the application of the composition in a cosmetic or medical use.

In one embodiment, said dialysis step (iv) comprises steps (iv.1) to (iv.3):
(iv.1) extruding the product obtained in step (ii) or step (iii) through a first sieve having a mesh size in the range of from 325 to 425 µm; and subsequently extruding the extruded product from the first sieve through a second sieve having a mesh size in the range of from 175 to 225 µm; and subsequently extruding the extruded product from the second sieve through a third sieve having a mesh size in the range of from 110 to 170 µm;
(iv.2) filling the product obtained in step (iv.1) into a dialysis membrane having a molecular weight cut off in the range of from 12,000 to 14,000 Da;
(iv.3) subjecting the filled membrane obtained in step (iv.2) to a dialysis solution.

In one embodiment, the gel obtained in step (ii) or step (iii) is extruded through a first sieve or screen having a mesh size of approximately 380 µm, such as 381 µm (0.015"), then through a second sieve or screen having a mesh size of approximately 200 µm, such as 203.2 µm (0.008"), then through a third sieve or screen having a mesh size of approximately 140 µm, such as 139.7 µm (0.0055"), into the dialysis membranes. The filled dialysis membrane or filled membranes are then placed into a container containing a suitable dialysis solution, such as the buffer solution used according to the first aspect of the invention with respect to step (i).

In one embodiment, if a blending step (iii) is performed after step (ii) and prior to dialysis step (iv), step (iii) facilitates the sieving steps, which are performed after step (iv) according to step (iv.1).

In one embodiment, dialysis is performed by stirring the content of the container. In one embodiment, the dialysis solution may be exchanged once or at least twice by a fresh dialysis solution. In one embodiment, the interval of exchange ranges from 8 to 18 hours, or from 10 to 14 hours, such as 12±2 hours. In one embodiment, dialysis according to step (iv) is allowed to proceed for 30 to 45 hours, or from 35 to 39 hours, such as 3±2 hours.

In one embodiment, tan δ of the composition obtained in step (iv) ranges from 0.1 to 0.9 measured at a frequency of 0.7 Hz and 30° C. such as from 0.1 to 0.5, or from 0.2 to 0.4.

In another embodiment, tan δ of the composition obtained in step (iv) ranges from 0.1 to 3.5 measured at a frequency of 0.7 Hz and 30° C.

In one embodiment, η* is in the range of from 2,000 mPa*s to 200,000 mPa*s at a frequency of 0.7 Hz and 30° C., wherein tan δ ranges from 0.1 to 0.9, such as from 0.1 to 0.5, or from 0.2 to 0.4.

In one embodiment, tan δ of the composition obtained in step (iv) ranges from 0.10 to 3.5 measured at a frequency of 0.7 Hz and 30° C. In one embodiment, corresponding viscosity η* is in the range of from 2,500 mPa*s to 145,000 mPa*s, or from 4,000 to 145,000 mPa*s.

In one embodiment, tan δ of the composition obtained in step (iv) ranges from 0.10 to 3.5 measured at a frequency of 0.7 Hz and 30° C. In one embodiment, tan δ of the composition obtained in step (iv) ranges from 0.10 to 0.25 measured at a frequency of 0.7 Hz and 30° C.

Step (v)

Although the composition according to the invention allows for an use, which avoids adverse skin reaction as far as possible, in one embodiment, a local anesthetic and/or anti-arrhythmic drug may be added to the composition or gel according to the invention obtained in step (iv), if necessary or desired. Such drug may relieve itching, burning and pain, which might arise from skin inflammation when the composition or gel according to the invention is injected into skin tissue.

Suitable drugs are known in the art.

In one embodiment, lidocaine is used as a local anesthetic and/or anti-arrhythmic drug. This drug is known for e.g. injection as a dental anesthetic or as a local anesthetic for minor surgery.

In one embodiment, lidocaine is used in the form of a salt such as the hydrochloride and/or in the form of a hydrate such as the monohydrate.

Accordingly, the term "lidocaine" as used herein, encompasses the salts and hydrates thereof.

In one embodiment, lidocaine is used in an amount of from 0 to 1% by weight based on the weight of the composition or gel, or from 0 to 0.5 wt.-%.

In one embodiment, the weight is from 0.3% to 0.35%.

In one embodiment, the weight is 0.3% or is 0.35%.

In another embodiment, tetracaine is used. The term "tetracaine" as used herein, encompasses the salts and hydrates thereof. Tetracaine may be used in the same quantities as lidocaine.

In another embodiment, a mixture of lidocaine and tetracaine is used,

Accordingly, in one embodiment, the method according to the invention further comprises step (v) after step (iv):

(v) admixing an anesthetic or anti-arrhythmic or an anesthetic and anti-arrhythmic to the product obtained in step (iv).

In one embodiment, the method according to the invention further comprises step (v) after step (iv):

(v) admixing lidocaine, or lidocaine hydrochloride, or lidocaine hydrochloride monohydrate to the product obtained in step (iv); or admixing tetracaine to the product obtained in step (iv); or admixing lidocaine and tetracaine to the product obtained in step (iv).

In one embodiment, tan $\delta$ of the composition obtained in step (v) ranges from 0.1 to 0.9 measured at a frequency of 0.7 Hz and 30° C. such as from 0.1 to 0.5, or from 0.2 to 0.4.

In another embodiment, tan $\delta$ of the composition obtained in step (v) ranges from 0.1 to 3.5 or from 0.15 to 3.4 measured at a frequency of 0.7 Hz and 30° C.

In one embodiment, $\eta^*$ is in the range of from 2,000 mPa*s to 200,000 mPa*s at a frequency of 0.7 Hz and 30° C., wherein tan $\delta$ ranges from 0.1 to 0.9, such as from 0.1 to 0.5, or from 0.2 to 0.4.

In one embodiment, tan $\delta$ of the composition obtained in step (v) ranges from 0.10 to 3.5 measured at a frequency of 0.7 Hz and 30° C. In one embodiment, corresponding viscosity $\eta^*$ is in the range of from 2,500 mPa*s to 145,000 mPa*s, or from 4,000 to 145,000 mPa*s.

In one embodiment, tan $\delta$ of the composition obtained in step (v) ranges from 0.10 to 3.5 measured at a frequency of 0.7 Hz and 30° C. In one embodiment, tan $\delta$ of the composition obtained in step (v) ranges from 0.10 to 0.25 measured at a frequency of 0.7 Hz and 30° C.

In one embodiment, tan $\delta$ of the composition obtained in step (v) ranges from 0.1 to 3.5 measured at a frequency of 0.7 Hz and 30° C. In one embodiment, corresponding viscosity $\eta^*$ is in the range of from 2,000 mPa*s to 150,000 mPa*s. In one embodiment, tan $\delta$ of the composition obtained in step (v) ranges from 0.15 to 3.5 measured at a frequency of 0.7 Hz and 30° C. In one embodiment, corresponding viscosity $\eta^*$ is in the range of from 2,500 mPa*s to 145,000 mPa*s, or from 4,000 to 145,000 mPa*s.

In one embodiment, tan $\delta$ of the composition obtained in step (v) ranges from 0.15 to 0.25 measured at a frequency of 0.7 Hz and 30° C. In one embodiment, the corresponding viscosity $\eta^*$ is in the range of from 15,000 mPa*s to 28,000 mPa*s.

Step (vi)

Finally, in one embodiment, the product obtained in step (iv) or step (v) may be filled into a syringe. This is since the product obtained in the method according to the invention is intended to be injected for application In one embodiment, the product obtained in step (iv) or step (v) is filled into a syringe, and is sterilized.

Accordingly, in one embodiment, the method according to the invention further comprises step (vi) after step (iv) or step (v):

(vi) filling the product obtained in step (iv) or step (v) into a syringe and sterilizing it.

In one embodiment, the product obtained in step (iv) or step (v) is extruded into the syringe, whereby the filling is effected.

Sterilization may be effected by methods known in the art. The term "sterilization" as used herein encompasses any process that eliminates or removes or kills all forms of microbial life, including transmissible agents (such as fungi, bacteria, viruses, spore forms, etc.) present on the surface of the syringe and/or in the composition or gel prepared according to the method of the invention Sterilization may be achieved by the methods known in the art such as applying heat, chemicals, irradiation, high pressure or filtration, or a proper combination thereof.

In one embodiment, sterilization is effected prior to the filling according to step (vi), i.e. the composition or gel obtained in step (iv), or obtained in step (v), and the syringe are sterilized independently from one another.

In another embodiment, sterilization is effected during the filling according to step (vi).

In another embodiment, sterilization is effected after the filling according to step (vi).

In one embodiment, the overall content of HA in the final composition, such as the gel, is in the range of from 1 to 5% by weight based on the total weight of the composition. In another embodiment, the overall content is in the range of from 1.5 to 4% by weight, or from 2 to 2.5% by weight.

In one embodiment, the product obtained according to step (iv), or obtained according to step (v), or obtained according to step (vi), is an isotonic, sterile, viscoelastic composition such as a gel. This composition or gel is injectable and may act as an implant to increase the volume of skin tissue, i.e. to augment it.

In one embodiment, the product obtained according to step (iv), or obtained according to step (v), or obtained according to step (vi), is an isotonic, sterile, viscoelastic injectable gel or implant to increase the volume of e.g. face skin tissue, or to correct moderate or deep wrinkles.

In one embodiment, the skin tissue comprises or is the tissue of the lips.

In another embodiments, the skin tissue comprises or is the skin tissue of moderate to severe facial wrinkles or folds, such as nasolabial folds.

In one embodiment, the composition prepared according to the first aspect of the invention, provides for a safe and effective, biocompatible, non-immunogenic composition, which is easy to distribute and store, and which should not require allergy testing. Additionally, the composition has an acceptable persistency when applied to skin tissue. In one embodiment, the composition prepared according to the method of the invention is stable for a considerable time period, when applied to skin tissue.

Accordingly, in one embodiment, the invention relates to a method of preparing a composition according to the first aspect, or according to the method of the first aspect and any embodiment or any combination of at least two embodiments defined therein, wherein the composition obtained in step (iii) is dialyzed in step (iv) such to have a $p_H$ in the range of from 6.5 to 7.5 such as 6.7 to 7.2, or from 6.8 to 7.1 or from 6.8 to 6.9.

In one embodiment, the invention relates to a method of preparing a composition according to the first aspect, or according to the method of the first aspect and any embodiment or any combination of at least two embodiments defined therein, wherein the gel obtained in step (iii) is dialyzed in step (iv) such to have a swellability in the range of from 5 to 25% based on the total weight of the gel, such as from 6 to 23% or from 7 to 22% or from 9 to 21%.

In one embodiment, the invention relates to a method of preparing a composition according to the first aspect, or according to the method of the first aspect and any embodiment or any combination of at least two embodiments defined therein, wherein tan δ of the composition obtained in step (iv) or step (v) ranges from 0.1 to 0.9 measured at a frequency of 0.7 Hz and 30° C. and/or viscosity $\eta^*$ is in the range of from 2,000 mPa*s to 200,000 mPa*s; or ranges from 0.1 to 3.5 measured at a frequency of 0.7 Hz and 30° C. and/or viscosity $\eta^*$ is in the range of from 2,000 mPa*s to 150,000 mPa*s; or tan δ of the composition obtained in step (iv) or step (v) ranges from 0.15 to 3.5 measured at a frequency of 0.7 Hz and 30° C. and/or viscosity $\eta^*$ is in the range of from 2,100 mPa*s to 145,000 mPa*s, or from 2,500 to 145,000 mPa*s, or from 4,000 to 145,000 mPa*s, measured at a frequency of 0.7 Hz and 30° C.; or tan δ of the composition obtained in step (iv) or step (v) ranges from 0.10 to 0.25 measured at a frequency of 0.7 Hz and 30° C. and/or viscosity $\eta^*$ is in the range of from 15,000 mPa*s to 28,000 mPa*s measured at a frequency of 0.7 Hz and 30° C.; or tan δ of the composition obtained in step (iv) or step (v) ranges from 0.10 to 0.25 measured at a frequency of 0.7 Hz and 30° C. and/or viscosity $\eta^*$ is in the range of from 22,000 mPa*s to 28,000 mPa*s measured at a frequency of 0.7 Hz and 30° C.

In one embodiment, the invention relates to a method of preparing a composition according to the first aspect, or according to the method of the first aspect and any embodiment or any combination of at least two embodiments defined therein, wherein the composition, when injected into skin tissue, is stable for at least three months, such as for at least 4 months, or five months, or six months.

In one embodiment, the invention relates to a method of preparing a composition according to the first aspect, or according to the method of the first aspect and any embodiment or any combination of at least two embodiments defined therein, wherein said anesthetic and/or anti-arrhythmic, such as lidocaine or tetracaine, or lidocaine and tetracaine of step (v), is released when injected into skin tissue; and wherein the composition is sterile.

In one embodiment, the invention relates to a method of preparing a composition according to the first aspect, or according to the method of the first aspect and any embodiment or any combination of at least two embodiments defined therein, wherein the overall content of HA in the final composition, such as a gel, is in the range of from 1 to 5% by weight based on the total weight of the composition, such as from 1.5 to 4% by weight, or from 2 to 2.5% by weight.

In one embodiment, the invention relates to a method of preparing a composition according to the first aspect, or according to the method of the first aspect and any embodiment or any combination of at least two embodiments defined therein, wherein the composition does not irritate skin tissue when injected into said skin tissue.

In one embodiment, the invention relates to a method of preparing a composition according to the first aspect, or according to the method of the first aspect and any embodiment or any combination of at least two embodiments defined therein, wherein the composition is used as an injectable tissue filler while the composition is in the form of a gel.

In one embodiment, the invention relates to a method of preparing a composition according to the first aspect, or according to the method of the first aspect and any embodiment or any combination of at least two embodiments defined therein, wherein the hyaluronic acid, or the hyaluronic acid and the anesthetic and/or anti-arrhythmic, are the only active ingredients of the composition.

According to a second aspect, the invention relates to a composition, such as a gel, comprising a crosslinked first polymer, optionally a second polymer, which may be crosslinked or non-crosslinked, and water, wherein the first and the second polymer are selected from a polysaccharide such as HA.

In one embodiment, the composition, such as a gel, comprising a crosslinked first polymer, optionally a second polymer, which may be crosslinked or non-crosslinked, and water, wherein the first and the second polymer are selected from a polysaccharide, is obtainable by the method according to the first aspect of the invention, or is obtainable by the method according to the first aspect and any embodiment or any combination of at least two embodiments defined therein.

In one embodiment, the composition, such as a gel, consisting of a crosslinked first polymer, optionally a second polymer, which may be crosslinked or non-crosslinked, and water, and optionally an anesthetic and/or anti-arrhythmic, wherein the first and the second polymer are selected from a polysaccharide, is obtainable by the method according to the first aspect of the invention, or is obtainable by the method according to the first aspect and any embodiment or any combination of at least two embodiments described therein.

According to a third aspect, the invention relates to a kit, the kit comprising a syringe and the composition, such as a gel, according to the second aspect, or a syringe and the composition, such as a gel, prepared according to the method according to the first aspect.

According to a fourth aspect, the invention relates to the use of the composition, such as a gel, according to the second aspect, or to the composition, such as a gel, prepared according to the first aspect, in a cosmetic application.

In one embodiment, the composition, such as a gel, is used as a dermatological filler.

The term "dermatological filler" as used herein means that the composition such as a gel prepared according to the invention is suitable for increasing the volume of skin tissue, i.e. to augment skin tissue.

In one embodiment, the composition such as a gel is used to augment skin tissue such as to augment skin face tissue, and/or to correct moderate or deep wrinkles.

In one embodiment, the composition is an injectable composition, i.e. it is injected into skin tissue when applied.

According to a further aspect, the composition according to the second aspect may be used as a pharmaceutical composition or in a pharmaceutical composition In one embodiment, the composition is used in medical applications, which require the use of compositions, such as gels, based on hyaluronic acid.

Thus, according to a fifth aspect, the invention relates to a composition, such as a gel, according to the second aspect for use as a medicament.

According to a sixth aspect, the invention relates to a method of preparing a composition, such as a gel, the composition comprising a crosslinked first polymer, and optionally a second polymer, the second polymer may be crosslinked or non-crosslinked, and water, wherein the first and the second polymer are selected from a polysaccharide, the method comprising at least a first sieving step (a).

The term "sieving step" encompasses a step in which a crosslinked polymer, such as a crosslinked hyaluronic acid, and water, are extruded through a sieve.

In one embodiment, the term "sieving step" encompasses a step in which a product obtained in any one of steps (i) to (vi) as defined with respect to the first aspect of the invention is extruded through a sieve. The term "extruded through a sieve" as e.g. mentioned under the first aspect of the invention encompasses terms such as "passed through a sieve", or "pressed through a sieve" or "directed through a sieve" or "filtered".

The term "sieve" encompasses the term "filter".

The term "sieve" or "filter" encompasses any device having pores or holes through which a liquid may penetrate, wherein particles, which may be contained in the liquid, may be removed or which may be sheared to fit through the pores of the sieve or the filter. Thus, in one embodiment, the particles are resized by sieving or filtering. The sieve may e.g. be provided in the form of a net of metal wires or fibers such as plastic fibers. Suitable sieves are known in the field of sieving and filtering.

In one embodiment, the method comprises at least a second sieving step (b).

In another embodiment, the method comprises besides the first sieving step (a) and the second sieving step (b) at least a third sieving step (c).

In another embodiment, the method comprises besides the first sieving step (a) and the second sieving step (b) and the third sieving step (c) at least one further sieving step, or at least two further sieving steps, or at least three further sieving steps, or at least four further sieving steps.

In one embodiment, the second sieving step (b) is performed using a second sieve having a mesh size that is less than the mesh size of a first sieve that is used in the first sieving step (a).

In another embodiment, the third sieving step (c) is performed using a third sieve having a mesh size that is less than the mesh size of the second sieve used in the second sieving step (b).

In another embodiment, the third sieving step (c) is performed using a third sieve having a mesh size that is less than the mesh size of the second sieve used in the second sieving step (b), which in turn has a mesh size that is less than the mesh size of the first sieve used in the first sieving step (a).

In still another embodiment, each subsequently used sieve has a mesh size that is less than the mesh size of a sieve used in the preceding sieving step.

In one embodiment, the first sieve has a mesh size in the range of from 200 to 600 µm.

In another embodiment, the first sieve has a mesh size in the range of from 200 to 600 µm; and the second sieve has a mesh size in the range of from 100 to 400 µm.

In still another embodiment, the first sieve has a mesh size in the range of from 200 to 600 µm; and the second sieve has a mesh size in the range of from 100 to 400 µm; and the third sieve has a mesh size in the range of from 50 to 300 µm.

In one embodiment, the first sieve has a mesh size in the range of from 300 to 500 µm.

In another embodiment, the first sieve has a mesh size in the range of from 300 to 500 µm; and the second sieve has a mesh size in the range of from 100 to 300 µm.

In still another embodiment, the first sieve has a mesh size in the range of from 300 to 500 µm; and the second sieve has a mesh size in the range of from 100 to 300 µm; and the third sieve has a mesh size in the range of from 50 to 200 µm.

In one embodiment, the first sieve has a mesh size in the range of from 325 to 425 µm.

In another embodiment, the first sieve has a mesh size in the range of from 325 to 425 µm; and the second sieve has a mesh size in the range of from 175 to 225 µm.

In another embodiment, the first sieve has a mesh size in the range of from 325 to 425 µm; and the second sieve has a mesh size in the range of from 175 to 225 µm; and the third sieve has a mesh size in the range of from 110 to 170 µm.

In one embodiment, the sieving according to at least one of the sieving steps (a), (b) or (c) is performed at a temperature of from 5 to 30° C. such as 5 to 25° C. or 5 to 20° C. or 5 to 15° C. or 5 to 10° C.

In one embodiment, prior or subsequent to the first sieving step (a), or prior or subsequent to the second sieving step (b), or prior or subsequent to the third sieving step (c), the method comprises at least one of the following steps (i) to (vi) as defined with respect to the first aspect of the invention.

Accordingly, in one embodiment of the sixth aspect, prior or subsequent to the first sieving step (a), or prior or subsequent to the second sieving step (b), or prior or subsequent to the third sieving step (c), the method comprises at least one of the following steps (i) to (vi):

(i) crosslinking a mixture comprising the first polymer and water;
(ii) subsequent to the crosslinking in step (i), terminating the crosslinking;
(iii) optionally blending the product obtained in step (ii) with the second polymer;
(iv) subjecting the product obtained in step (ii), or step (iii) to dialysis;
(v) admixing an anesthetic and/or anti-arrhythmic such as lidocaine, or lidocaine hydrochloride, or lidocaine hydrochloride monohydrate, or tetracaine, or lidocaine and tetracaine, to the product obtained in step (iv);
(vi) filling the product obtained in step (v) into a syringe and sterilizing it.

In another embodiment, prior or subsequent to the first sieving step (a), or prior or subsequent to the second sieving step (b), or prior or subsequent to the third sieving step (c), the method comprises at least one of the following steps (i) to (vi):

(i) crosslinking a mixture comprising the first polymer and water;
(ii) subsequent to the crosslinking in step (i), terminating the crosslinking;
(iii) optionally blending the product obtained in step (ii) with the second polymer;
(iv) subjecting the product obtained in step (i), or step (ii), or step (iii) to dialysis;
(v) admixing an anesthetic and/or anti-arrhythmic such as lidocaine, or lidocaine hydrochloride, or lidocaine hydrochloride monohydrate, or tetracaine, or lidocaine and tetracaine, to the product obtained in step (i), or step (ii), or step (iii), or step (iv);

(vi) filling the product obtained in step (i), or step (ii), or step (iii), or step (iv), or step (v) into a syringe and sterilizing it.

In one embodiment, the first sieving step (a) is performed subsequently to step (i).

In another embodiment, the first sieving step (a) and the second sieving step (b) are performed subsequently to step (i).

In still another embodiment, the first sieving step (a) and the second sieving step (b) and the third sieving step (c) are performed subsequently to step (i).

In one embodiment, the first sieving step (a) is performed subsequently to step (ii).

In another embodiment, the first sieving step (a) and the second sieving step (b) are performed subsequently to step (ii).

In still another embodiment, the first sieving step (a) and the second sieving step (b) and the third sieving step (c) are performed subsequently to step (ii).

In one embodiment, the first sieving step (a) is performed subsequently to step (iii).

In another embodiment, the first sieving step (a) and the second sieving step (b) are performed subsequently to step (iii).

In still another embodiment, the first sieving step (a) and the second sieving step (b) and the third sieving step (c) are performed subsequently to step (iii).

In one embodiment, the first sieving step (a) is performed subsequently to step (iv).

In another embodiment, the first sieving step (a) and the second sieving step (b) are performed subsequently to step (iv).

In still another embodiment, the first sieving step (a) and the second sieving step (b) and the third sieving step (c) are performed subsequently to step (iv).

In one embodiment, the first sieving step (a) is performed subsequently to step (v).

In another embodiment, the first sieving step (a) and the second sieving step (b) are performed subsequently to step (v).

In still another embodiment, the first sieving step (a) and the second sieving step (b) and the third sieving step (c) are performed subsequently to step (v).

The use of sieves supports the removal of extraneous compounds and particles such as gelled particles, which may negatively affect the desired homogeneity of the product, or helps to resize the particles to fit through the pores of the sieve by applying shear forces. Thus, in one embodiment, a sieving step or several sieving steps used in the method according to the invention allow(s) for the preparation of a particularly homogeneous composition, i.e. a particularly homogeneous gel comprising the first polymer, optionally a second polymer, and water. Homogeneity supports and improves the intended application such as the application of the composition in a cosmetic or medical use.

According to a seventh aspect, the invention relates to a composition, such as a gel, the composition comprising a crosslinked first polymer, and optionally a second polymer, the second polymer may be crosslinked or non-crosslinked, and water, wherein the first and the second polymer are selected from a polysaccharide, prepared or obtainable by a method as defined in the sixth aspect of the invention, or in any one of the embodiments or in any one of at least two embodiments defined in the sixth aspect.

According to an eighth aspect, the invention relates to a kit, the kit comprising a syringe and the composition prepared or obtainable by a method as defined in the sixth aspect of the invention, or in any one of the embodiments of the sixth aspect; or to a kit comprising a syringe and a composition as defined in the seventh aspect of the invention.

According to a ninth aspect, the invention relates to the use of the composition prepared or obtainable by a method as defined in the sixth aspect of the invention, or in any one of the embodiments or in any one of at least two embodiments defined in the sixth aspect; or to the use of the composition as defined in the seventh aspect of the invention, in a cosmetic application; or as a dermatological filler.

According to a tenth aspect, the invention relates to a composition, such as a gel, the composition comprising a crosslinked first polymer, and optionally a second polymer, the second polymer may be crosslinked or non-crosslinked, and water, wherein the first and the second polymer are selected from a polysaccharide, prepared or obtainable by a method as defined in the sixth aspect of the invention, or in any one of the embodiments or in any one of at least two embodiments defined in the sixth aspect, or to a composition as defined in the seventh aspect of the invention, for use as a medicament.

According to an eleventh aspect, the invention relates to the use of at least one sieve or at least one sieving step in the preparation of a composition comprising a crosslinked hyaluronic acid and water.

In one embodiment of this use, at least two sieves or two sieving steps are used.

In another embodiment, at least three sieves are or at least three sieving steps are used.

EXAMPLES

Example 1

Preparation of Buffer Solution

A buffer solution is made from sodium chloride, dibasic anhydrous sodium phosphate, monobasic sodium phosphate dihydrate and water by dissolving the salts in water.

Preparation of HA in Buffer

Subsequent to the preparation of the buffer solution, sodium hyaluronate having a molecular weight of from 2.5 MDa to less than 3.0 MDa is added to a quart mixing bowl and a portion of the buffer solution is added to it. The contents are mixed for 2.0 to 2.5 hours using a stirrer at 250 rpm while the jacket setpoint on the mixing bowl is set to 50° C. Subsequent to the mixing, the contents are then cooled to 5 to 7° C.

Addition of Alkaline Solution

A first alkaline solution is prepared by dissolving sodium hydroxide in the above buffer solution. Then, a second alkaline solution is prepared by dissolving sodium hydroxide in the above buffer solution. The first alkaline solution is then added to the contents in the mixing bowl and the contents are mixed for 30 to 40 minutes at 250 rpm at a 5° C. jacket set point.

Crosslinking Reaction [Step (i)]

The crosslinking solution is prepared by adding BDDE to a portion of the second alkaline buffer solution. This alkaline solution comprising the crosslinking agent BDDE is added to the contents in the mixing bowl and allowed to mix for 10 to 15 minutes at 500 rpm at a 5° C. jacket setpoint. The mixing speed is then lowered to 100 rpm and the temperature set point is changed to a temperature of 30° C. After a temperature of 28° C. has been reached, the mixing is turned off, and the contents are allowed to set for approx. 3 hours.
Preparation of a Quench Solution for the Termination of the Crosslinking Reaction A 1 m HCl solution is added to a portion of the buffer solution to create a quench solution.
Quenching Reaction [Step (ii)]

The temperature setpoint on the jacket is set to 5° C. and the quench solution is added to the bowl contents. The contents are then mixed for 10 to 15 minutes at 500 rpm.
Processing of the Crosslinked HA The polymer resulting from step (ii) is then cut into pieces, which may be formed as chunks or strips. The size of the chunks or stripes may be 1.27 cm×1.27 cm×1.27 cm (0.5×0.5×0.5 inches) or smaller. The chunks or strips are then mixed for approximately 2.5 to 3.0 hours at 150 rpm at a 5° C. jacket setpoint. Subsequent to the mixing, the mixed product is extruded through a 558.8 µm µm [0.022"] screen and placed back into the mixing bowl and further mixed for 2.0 to 2.5 hours at 150 rpm at a 5° C. jacket setpoint.
Provision of the Second Polymer HA (sodium salt) having Mw 3.0 MDa is added to a portion of the buffer solution. The contents are mixed with an overhead mixer for a short period of time.
Preparation of a Gel [Step (iii)]

A portion of the second polymer in the buffer (1% w/w) is added to the contents in the quart mixer. The contents are allowed to mix for 1 to 5 min at 250 rpm.
Dialysis Reaction [Step (iv)]

Dialysis membranes having a MWCO of from 12,000 to 14.000 Da are hydrated in sterile water. Then, the gel obtained in step (iii) is extruded through a screen having a mesh size of approximately 380 µm, such as 381 µm (0.015"), then through a screen having a mesh size of approximately 200 µm, such as 203.2 µm (0.008"), then through a screen having a mesh size of approximately 140 µm, such as 139.7 µm (0.0055"), into the dialysis membranes. The dialysis membranes are filled and have an effective length of approximately 20.3 cm (8 inches) and an overall length of approximately 25.4 cm (10 inches). The membranes are then placed into a container containing the above buffer solution. The container is cooled down to 5° C. setpoint and the content is stirred. The dialysis solution is exchanged twice at an interval of 12±2 hours. The dialysis is allowed to proceed for 37±2 hours.
Extrusion of the Product Obtained in Step (iv) [Step (vi)]

After dialysis the membranes are combined, mixed and extruded twice through a sieve having a mesh size of approximately 140 µm, such as 139.7 µm (0.0055"), and are then further mixed for 30 to 40 min under vacuum. The resulting material is extruded into syringes and is steam sterilized.

The product obtained after step (iv) and contained in the syringe after step (vi) is an isotonic, sterile, viscoelastic injectable gel. This gel may be used as an implant suitable to increase the volume of e.g. face skin tissue, i.e. to augment said skin tissue, and/or to correct moderate or deep wrinkles of the skin.

Example 2

The reaction is performed according to Example 1 with the difference in crosslinking step (i):

The crosslinking solution is prepared by adding BDDE to a portion of the second alkaline buffer solution. This alkaline solution comprising the crosslinking agent BDDE is added to the contents in the mixing bowl and allowed to mix for 10 to 15 minutes at 500 rpm at a 5° C. jacket setpoint. The mixing speed is then lowered to 100 rpm and the temperature set point is changed to a temperature of 33.33° C. After a temperature of 31.33° C. has been reached, the mixing is turned off, and the contents are allowed to set for approx. 3 hours.

The product obtained after step (iv) and contained in the syringe after step (vi) is an isotonic, sterile, viscoelastic injectable gel. This gel may be used as an implant suitable to increase the volume of e.g. face skin tissue, i.e. to augment said skin tissue, and/or to correct moderate or deep wrinkles of the skin. This gel has a higher elasticity and viscosity than the gel according to Example 1.

Example 3

The reaction is performed according to Example 1 with the difference that an anesthetic and anti-arrhythmic such as lidocain is added to the gel obtained after step (iii):
Lidocaine Addition [Step (v)]

A solution of lidocaine HCl monohydrate is dissolved in the buffer solution and is added to the dialysis membranes containing the gel prepared according to step (iii) in an amount of 0.35 wt.-% based on gel. The contents may be extruded twice through a sieve having a mesh size of approximately 140 µm, such as 139.7 µm (0.0055"), and are then further mixed for 30 to 40 min under vacuum.

The product obtained after step (v) and contained in the syringe after step (vi) is an isotonic, sterile, viscoelastic injectable gel. This gel may be used as an implant suitable to increase the volume of e.g. face skin tissue, i.e. to augment said skin tissue, and/or to correct moderate or deep wrinkles of the skin.

Example 4

The reaction is performed according to Example 1 with the difference in crosslinking step (i):

The crosslinking solution is prepared by adding BDDE to a portion of the second alkaline buffer solution. This alkaline solution comprising the crosslinking agent BDDE is added to the contents in the mixing bowl and allowed to mix for 10 to 15 minutes at 500 rpm at a 5° C. jacket setpoint. The mixing speed is then lowered to 100 rpm and the temperature set point is changed to a temperature of 27° C. After a temperature of 25° C. has been reached, the mixing is turned off, and the contents are allowed to set for approx. 3 hours.

The product obtained after step (iv) and contained in the syringe after step (vi) is an isotonic, sterile, viscoelastic injectable gel. This gel may be used as an implant suitable to increase the volume of e.g. face skin tissue, i.e. to augment said skin tissue, and/or to correct moderate or deep wrinkles of the skin. This gel has a lower elasticity and viscosity than the gel according to Example 1.

Example 5

The reaction is performed according to Example 1 with the difference in crosslinking step (i) and blending step (iii):

The crosslinking solution is prepared by adding BDDE to a portion of the second alkaline buffer solution. This alkaline solution comprising the crosslinking agent BDDE is added to the contents in the mixing bowl and allowed to mix for 10 to 15 minutes at 500 rpm at a 5° C. jacket setpoint. The mixing speed is then lowered to 100 rpm and the temperature set point is changed to a temperature of 30° C. After a temperature of 27° C. has been reached, the mixing is turned off, and the contents are allowed to set for approx. 3 hours.

Provision of the Second Polymer

HA (sodium salt) having Mw 3.0 MDa is added to a portion of the buffer solution. The contents are mixed with an overhead mixer for a short period of time.

Preparation of a Gel [Step (iii)]

A portion of the second polymer in the buffer (3% w/w) is added to the contents in the quart mixer. The contents are allowed to mix for 1 to 5 min at 250 rpm.

The product obtained after step (iv) and contained in the syringe after step (vi) is an isotonic, sterile, viscoelastic injectable gel. This gel may be used as an implant suitable to increase the volume of e.g. face skin tissue, i.e. to augment said skin tissue, and/or to correct moderate or deep wrinkles of the skin.

Example 6

The reaction is performed according to Example 1 with the difference in crosslinking step (i) and blending step (iii):

The crosslinking solution is prepared by adding BDDE to a portion of the second alkaline buffer solution. This alkaline solution comprising the crosslinking agent BDDE is added to the contents in the mixing bowl and allowed to mix for 10 to 15 minutes at 500 rpm at a 5° C. jacket setpoint. The mixing speed is then lowered to 100 rpm and the temperature set point is changed to a temperature of 25° C. After a temperature of 22° C. has been reached, the mixing is turned off, and the contents are allowed to set for approx. 3 hours.

Provision of the Second Polymer

HA (sodium salt) having Mw 3.0 MDa is added to a portion of the buffer solution. The contents are mixed with an overhead mixer for a short period of time. Subsequently, a portion of the crosslinking solution used in step (i) is added to the second polymer in the buffer solution.

Preparation of a Gel [Step (iii)]

A portion of the crosslinked second polymer in the buffer (1% w/w) is added to the contents in the quart mixer. The contents are allowed to mix for 1 to 5 min at 250 rpm.

The product obtained after step (iv) and contained in the syringe after step (vi) is an isotonic, sterile, viscoelastic injectable gel. This gel may be used as an implant suitable to increase the volume of e.g. face skin tissue, i.e. to augment said skin tissue, and/or to correct moderate or deep wrinkles of the skin.

Example 7

The reaction is performed according to Example 2 with the difference that an anesthetic and anti-arrhythmic such as lidocain is added to the gel obtained after step (iii):

Lidocaine Addition [Step (v)]

A solution of lidocaine HCl monohydrate is dissolved in the buffer solution and is added to the dialysis membranes containing the gel prepared according to step (iii) in an amount of 0.35 wt.-% based on gel. The contents may be extruded twice through a sieve having a mesh size of approximately 140 μm, such as 139.7 μm (0.0055"), and are then further mixed for 30 to 40 min under vacuum.

The product obtained after step (v) and contained in the syringe after step (vi) is an isotonic, sterile, viscoelastic injectable gel. This gel may be used as an implant suitable to increase the volume of e.g. face skin tissue, i.e. to augment said skin tissue, and/or to correct moderate or deep wrinkles of the skin.

Example 8

The reaction is performed according to Example 1 with the difference that after step (ii) blending step (iii) is omitted.

The product obtained after step (iv) and contained in the syringe after step (vi) is an isotonic, sterile, viscoelastic injectable gel. This gel may be used as an implant suitable to increase the volume of e.g. face skin tissue, i.e. to augment said skin tissue, and/or to correct moderate or deep wrinkles of the skin.

Examples 9 to 14

The reaction is performed according to Examples 2 to 7 with the difference that after step (ii) blending step (iii) is omitted.

The products that are respectively obtained after step (iv) and that are contained in the syringe after step (vi) are isotonic, sterile, viscoelastic injectable gels. Said gels may be used as an implant suitable to increase the volume of e.g. face skin tissue, i.e. to augment said skin tissue, and/or to correct moderate or deep wrinkles of the skin.

The invention claimed is:

1. A method of preparing a composition comprising a crosslinked first polymer and, optionally a second polymer, and water, the method comprising at least steps (i), (ii) and (iv) and, optionally step (iii):
   (i) crosslinking a mixture comprising the first polymer and water;
   (ii) subsequent to the crosslinking in step (i), terminating the crosslinking;
   (iii) optionally blending a product obtained in step (ii) with the second polymer;
   (iv) subjecting a product obtained in step (ii) or step (iii) to dialysis;

wherein the first polymer and the second polymer is selected from hyaluronic acid and salts thereof, and wherein the second polymer may be crosslinked or non-crosslinked, and wherein the dialysis step (iv) comprises steps (a) to (c):
   (a) extruding a product obtained in step (ii) or step (iii) through a first sieve and subsequently extruding the extruded product from the first sieve through a second sieve, wherein the mesh size of the second sieve is less than the mesh size of the first sieve; or extruding a product obtained in step (ii) or step (iii) through a first sieve, and subsequently extruding the extruded product from the first sieve through a second sieve, and subsequently extruding the extruded product from the second sieve through a third sieve, wherein the mesh size of the second sieve less than the mesh size of the first sieve, less than the mesh size of the second sieve; and wherein the mesh size of the first sieve is in a range of from 200 to 600 μm, the mesh size of the second sieve is in a range of from 100 to 400 μm, and the mesh size of the third sieve is in a range of from 50 to 300 μm;
   (b) filling a product obtained in step (a) into a dialysis membrane; and
   (c) subjecting the filled dialysis membrane obtained in step (b) to a dialysis solution.

2. The method of claim 1, wherein the first polymer and the second polymer may be the same or may be different from one another.

3. The method of claim 1, wherein the second polymer is non-crosslinked.

4. The method of claim 1, wherein the first polymer used in step (i) exhibits a molecular weight of from 2.5 MDa to less than 3.0 MDa.

5. The method of claim 1, wherein the second polymer used in step (iii) exhibits a molecular weight of at least 3.0 MDa.

6. The method of claim 1, wherein the weight of the second polymer based on the weight of the first polymer is less than 5% or is less than 4%.

7. The method of claim 1, wherein the weight of the second polymer based on the weight of the first polymer is in a range of from 0.01 to 5%, from 0.1 to 4%, from 0.1 to 2.5%, from 0.2 to 2.0%, or from 0.5 to 1.5%.

8. The method of claim 1, further comprising step (v):
   (v) admixing an anesthetic and/or anti-arrhythmic selected from lidocaine, lidocaine hydrochloride, lidocaine hydrochloride monohydrate, tetracaine, and combinations thereof, to the product obtained in step (iv).

9. The method of claim 8, further comprising a step of filling the product obtained in step (iv) or step (v) into a syringe and sterilizing it.

10. The method of claim 1, wherein step (ii) comprises step (ii.1), or steps (ii.1) and (ii.2):
    (ii.1) subjecting a product obtained in step (i) to an acid;
    (ii.2) extruding a product obtained in step (ii.1); or
    extruding a product obtained in step (ii.1) through a sieve; or
    extruding a product obtained in step (ii.1) through a sieve having a mesh size in the range of from 500 to 600 μm.

11. The method of claim 10, wherein the mesh size is 558.8 μm.

* * * * *